(12) United States Patent
Tu et al.

(10) Patent No.: US 6,346,105 B1
(45) Date of Patent: Feb. 12, 2002

(54) DEVICE FOR TREATING TISSUE AND METHODS THEREOF

(75) Inventors: Hosheng Tu; Steve Chun-Guang Tu, both of Tustin, CA (US)

(73) Assignee: Quantum Cor Incorporated, Dana Point, CA (US)

( * ) Notice: Subject to any disclaimer, the term of this patent is extended or adjusted under 35 U.S.C. 154(b) by 0 days.

(21) Appl. No.: 09/518,549

(22) Filed: Mar. 3, 2000

Related U.S. Application Data (63) Continuation-in-part of application No. 09/122,913, filed on Jul. 27, 1998, now Pat. No. 6,050,993.

(51) Int. Cl.$^7$ ............................................. A61B 18/14
(52) U.S. Cl. ............................ 606/41; 606/32; 606/39
(58) Field of Search ................................. 607/154–155

(56) References Cited

U.S. PATENT DOCUMENTS

| | | | | |
|---|---|---|---|---|
| 4,621,635 A | * | 11/1986 | Ali | 606/14 |
| 4,938,221 A | | 7/1990 | Tuffel | 128/401 |
| 5,203,863 A | * | 4/1993 | Bidoia | 606/140 |
| 5,462,559 A | * | 10/1995 | Ahmed | 606/140 |
| 5,570,692 A | * | 11/1996 | Morinaga | 600/453 |
| 5,578,047 A | * | 11/1996 | Taylor | 606/157 |
| 5,741,273 A | * | 4/1998 | O'Regan | 606/140 |
| 5,906,620 A | * | 5/1999 | Nakao et al. | 606/113 |

OTHER PUBLICATIONS

Saclarides TJ et al, "Evolving Trends in the Treatment of Anorectal Diseases" Diseases of the Colon & Rectum 42(10):1245–1252, (1999).

Griffith CDM et al., "Out–patient Treatment of Haemorrhoids with Bipolar Diathermy Coagulation" Br J. Surg 74:827 (1987).

Salvati EP, "Non operative Management of Hemorrhoids" Diseases of the Colon & Rectum 42(8):989–993 (1999).

Dennison AR et al., "The Management of Hemorrhoids" Am J Gastroenterology 84(5): 475–481 (1989).

Hussain JN "Hemorrhoids" Office Management of Common Anorectal Problems 26(1):35–51 (1999).

\* cited by examiner

*Primary Examiner*—Lee Cohen
*Assistant Examiner*—Hank M. Johnson (57) ABSTRACT

A medical device for treating the hemorrhoid, or reducing the dilatation of cellular tissues comprising ligating a hemorrhoid tissue and heating the hemorrhoid tissue. In one embodiment, an elongate tubular shaft comprises at least one coil loop electrode arrangement disposed at the distal end portion of the shaft, a RF energy generating source, and a method for deploying a dilated ligature element to effect the pressure therapy for the hemorrhoid tissues.

15 Claims, 6 Drawing Sheets

DEVICE FOR TREATING TISSUE AND METHODS THEREOF

CROSS-REFERENCE TO RELATED APPLICATIONS

This patent application is a continuation-in-part application of application Ser. No. 09/122,913, entitled "Medical Device and Methods for Treating Hemorrhoids" filed Jul. 27, 1998, now U.S. Pat. No. 6,050,993 and is incorporated herein by reference.

TECHNICAL FIELD OF THE INVENTION

The present invention generally relates to an improved medical device and methods for treating tissues, and more particularly, to such a medical device and methods for treating hemorrhoids and/or polyps in a patient by delivering RF energy to the lesion sites in association with a therapeutic pressure therapy of a ligation method.

BACKGROUND OF THE INVENTION

Hemorrhoids, or enlarged veins in the anal area, represent one of the most frequent and familiar anorectal problems seen in primary care office setting. Hemorrhoids occur reportedly in up to 80% to 90% of the US population (Hussain J N, *Office Management of Common Anorectal Problems* 1999; 26:35–51). The actual prevalence based on epidemiologic studies is more in the range of 40%. The prevalence of hemorrhoids increases with age whereas pregnancy is a common predisposing risk factor for the development of hemorrhoids.

The method of reducing the size of cellular tissues in situ has been used in the treatment of many diseases, or as an adjunct to surgical removal procedures. One method used requires heating the tissues, and causing them to shrink and tighten. It is often less traumatic than surgical procedures and may be the only alternative method, whereby other procedures are unsafe or ineffective. Ablative treatment devices have an advantage because of the use of a destructive energy that is rapidly dissipated and reduced to a non-destructive level by conduction and convection, to forces of circulating fluids and other natural processes.

Devices using microwave energy, radiofrequency energy (RF), ultrasonic energy, cryogenic means, laser energy, and tissues destructive substances have been used to destroy malignant, benign, and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave energy antenna, through a duct, to the area of treatment, and applying energy diffusively through the duct wall into the surrounding tissues in the targeted directions.

Of particular interest to the present invention are RF therapeutic protocols, which have been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency or other energy, when coupled with a temperature control mechanism, can be supplied precisely to the device-to-tissues contact site to obtain the desired temperature for treating a tissue.

Hemorrhoid is a varicose dilatation of a vein of the superior or inferior hemorrhoidal plexus, resulting from a persistent increase in venous pressure. The external hemorrhoid is a varicose dilatation of a vein of the inferior hemorrhoidal plexus, situated distal to the pectinate line and covered with modified anal skin. The internal hemorrhoid is a varicose dilatation of a vein of the superior hemorrhoidal plexus, originating above the pectinate line, and covered by mucous membrane. A more serious case of hemorrhoid, prolapsed hemorrhoid, is an internal hemorrhoid that has descended below the pectinate line and protruded outside the anal sphincter. One of the worst cases, strangulated hemorrhoid, is an internal hemorrhoid which has been prolapsed sufficiently and for long enough time for its blood supply to become occluded by the constricting action of the anal sphincter. Currently, surgical removal is the only method for treating strangulated hemorrhoid, which results in prolonged pain during recovery period. The management of hemorrhoids using conventional approaches has been reported by Dennison AR et al. *The American Journal of Gastroenterology* 1989; 84:475–481; by Saclarides T J et al. *Diseases of the Colon & Rectum* 1999; 42:1245–1252; by Griffith C D M et al. *British Journal of Surgery* 1987; 74:827; and by Salvati E P *Diseases of the Colon & Rectum* 1999; 42:989–993.

Taylor in U.S. Pat. No. 5,578,047 teaches a hemorrhoid-removing device. Tuffel in U.S. Pat. No. 4,938,221 teaches a hemorrhoid inflammation-reducing device by introducing a coolant for shrinking hemorrhoids. Neither of them discloses a medical device by using a suitable energy to treat a dilated vein to denature and/or shrink it. On the other hand, an alternative for hemorrhoid treatment is by surgically removing the dilated vein by a laser or other means. For a dilated vein, RF energy or other suitable energy can be applied for treating the tissues of the vascular walls, and causing them to shrink, necrosis, and tighten.

Imran in U.S. Pat. No. 5,281,218 entitled "Catheter having needle electrode for radiofrequency ablation" teaches a method using a needle electrode that is attached onto a catheter for radiofrequency ablation. Though a needle-like electrode is beneficial to ablate a tissue point for deep lesion, it is not disclosed that the particular needle electrode could possibly combine pressure therapy for proper contact with the target tissues. The "pressure therapy" is defined in this invention as application of an appropriate pressure onto the tissues by a medical device, in association with another therapy, such as a RF therapy.

Bidoia in U.S. Pat. No. 5,203,863 teaches an instrument for the ligation of hemorrhoids, which applies pressure to the root of the hemorrhoids. However, the ligature element only applies pressure locally, not on the entire inflammable hemorrhoid tissue. Furthermore, Bidoia does not disclose a combination of thermal therapy with pressure therapy to enhance the treatment of hemorrhoids or polyps.

Clinically, hemorrhoids are traditionally divided into four grades or degrees (as shown by Dennison AR et al., Salvati E P, and Hussain J N). Ligation alone approach for hemorrhoid management can only handle the first or some second grade hemorrhoids. For the higher-grade hemorrhoids, neither ligation alone approach nor thermal treatment alone approach is satisfactory.

Therefore, there is a need for an improved medical device and methods using a combination of ligation techniques and the thermal energy to treat a dilated vein or tissue, such as hemorrhoids while simultaneously applying ligation pressure therapy to the target tissue.

SUMMARY OF THE INVENTION

In general, it is an object of the present invention to provide a method and an improved medical device for generating heat, to treat the hemorrhoids, vascular vessels, or other cellular tissues. It is another object of the present invention to provide a method and a device for monitoring the temperature of the medical device, and to control the temperature by utilizing a temperature control mechanism and/or algorithm. The location of the temperature sensor means is preferably at close proximity of the electrode means of the medical device. It is still another object of this invention to provide a method and a device for treating hemorrhoids, vascular walls, or cellular tissues in a patient by applying appropriate pressure to the tissues either by the device itself or by a ligation means associated with the device. It is still a further object to ligate a hemorrhoid tissue and heat the hemorrhoid tissue as an enhanced treatment method.

Briefly, heat is generated by supplying a suitable energy source to a device, which comprises at least one electrode means, in contact with the body tissues. A suitable energy source may consist of radiofrequency energy, microwave energy, ultrasonic energy, infrared energy, alternating current energy, or laser energy. The energy can be applied to the hemorrhoids, vascular walls, or cellular tissues through the electrode means, wherein the electrode means in this invention refers to the metal element for radiofrequency energy, the antenna for microwave energy, the transducer for ultrasound energy, the bulb element for infrared energy, the fiber optic for laser energy, and the like. A DIP (dispersive indifferent pad) type pad or electrode, that contacts the patient, is connected to the Indifferent Electrode Connector on the RF generator for radiofrequency application. Therefore, the RF energy delivery becomes effective when a close circuit from a RF generator through a patient and returning to the RF generator is formed. When using an alternating current outlet, the generator should be grounded to avoid electrical interference. In the case of radiofrequency applications, heat is controlled by the power of the RF energy delivered, the delivery mode, and by the delivery duration. The standard RF energy generator and its applications through the electrode means, to a patient are well known for those who are skilled in the art.

In an optional embodiment, means for generating vibration at the distal section of the device comprises a motor mounted in a cavity of the handle of the device, which has a rotatable motor shaft, an elongated connecting shaft having a first end, to which the distal end portion is connected, and a second end connected to the handle, a weight eccentrically mounted on the motor shaft with respect to the motor shaft axis, so as to rotate eccentrically, so that when the motor shaft rotates, the distal end portion of the device vibrates.

In one embodiment, the device comprises at least one electrode means, wherein the electrode means composes a compressible coil arrangement or a plurality of compressible coils. The coil arrangement is connected to an external RF generating means through an electrical conductor. The contact surface of the coil arrangement to the target tissue is pre-shaped and/or maximized by either flattening the contact surface or by pre-shaping the contact surface in a concave or convex fashion to encircle the essentially round surface of the hemorrhoids and the like. The coil arrangement is compressible so that when the coil electrode is pressed against the tissues or the round surface of a hemorrhoid, an appropriate pressure is exerted onto the tissues while applying the RF energy therapy.

In another embodiment, an elastic dilated ligature element and the like is circumferentially and externally positioned at about the distal section of the delivery tubular shaft of the medical device at a non-deployed state, wherein the dilated ligature element may be pushed off the distal section of the delivery tubular shaft at a deployed state to ligate the root or other desired site of the hemorrhoid.

The method and medical device of the present invention has several significant advantages over other known systems or techniques to treat the hemorrhoids or polyps. In particular, the device system comprising the electrode means, using RF energy as a heat source and simultaneously applying pressure therapy via a dilated ligature element to the tissues, results in a more efficient therapeutic effect for hemorrhoids treatment.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 6, what is shown is an embodiment of the medical device system, comprising simultaneously applying a pressure therapy and applying radiofrequency energy to a ligated tissue for treating the hemorrhoids of a patient.

One of the treatment methods of internal hemorrhoids may use a conventional rubber band ligation technique. It involves placing a tiny rubber band around the base of an internal hemorrhoid, thereby devascularizing the prolapsing tissue, which undergoes necrosis and sloughes within 3 to 10 days. The ligation alone has several disadvantages, such as development of severe perianal sepsis, bleeding and a 15% to 20% recurrence rate of internal hemorrhoids within 5 years.

The medical device of the present invention combines applying heat to accelerate the tissue necrosis of the prolapsing tissue while ligate the base of the hemorrhoid so that the disadvantages of the above-mentioned ligation alone can be eliminated or substantially reduced. In one embodiment, a method of treating a hemorrhoid of a patient may comprise dual features of ligating a hemorrhoid tissue and heating the hemorrhoid tissue. This enhanced treatment method using a dual-feature device for hemorrhoids overcomes the disadvantages of either ligation alone method or thermal therapy alone method. The enhanced treatment method is more effective in treating the higher grades of hemorrhoids, such as the second, third, or fourth grade hemorrhoids.

Figure 1:
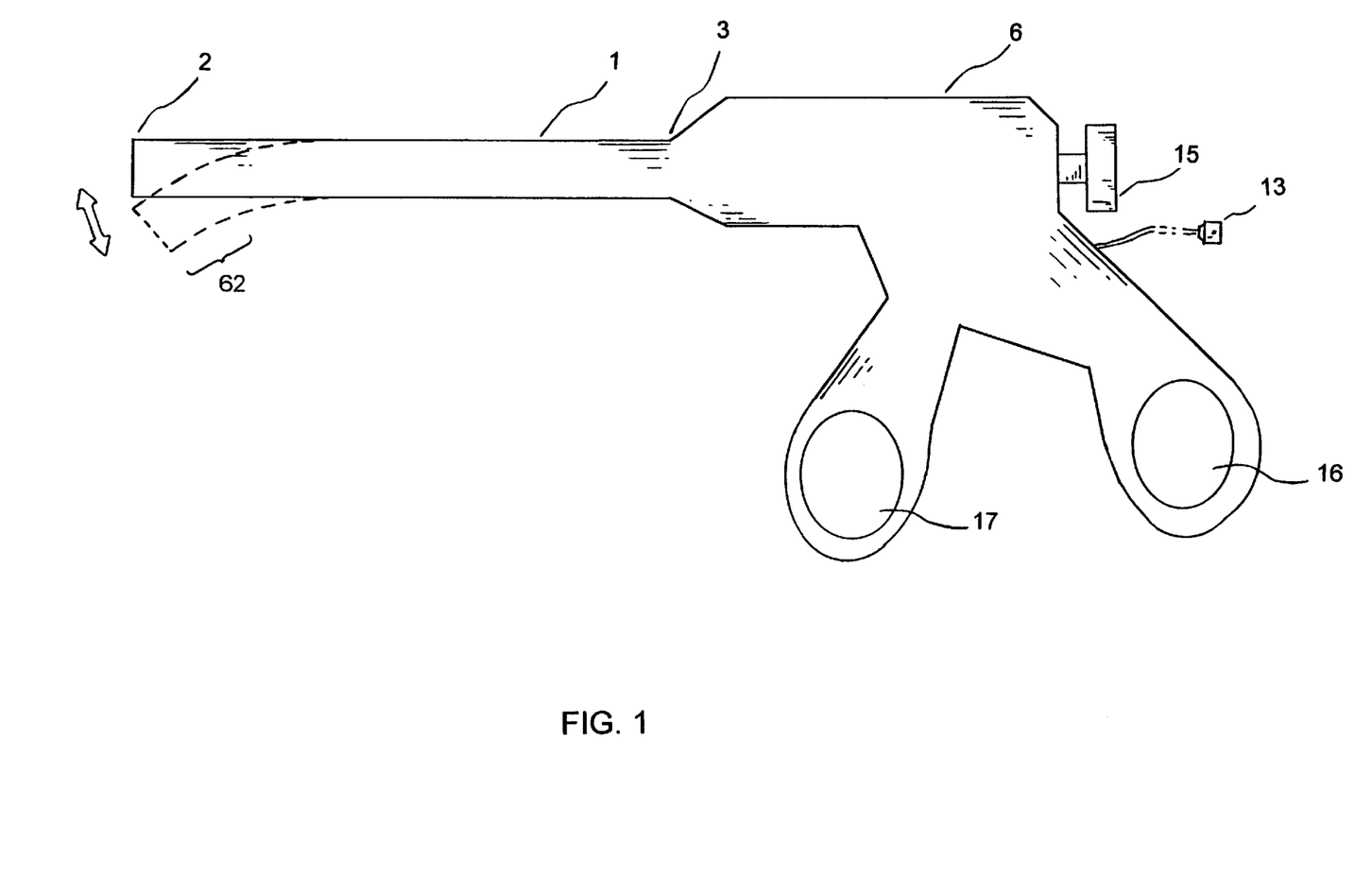
FIG. 1 is an overall view of a medical device, comprising an electrode means having a compressible, concave or convex-top coil arrangement, constructed in accordance with the principles of the present invention.
Figure 2:
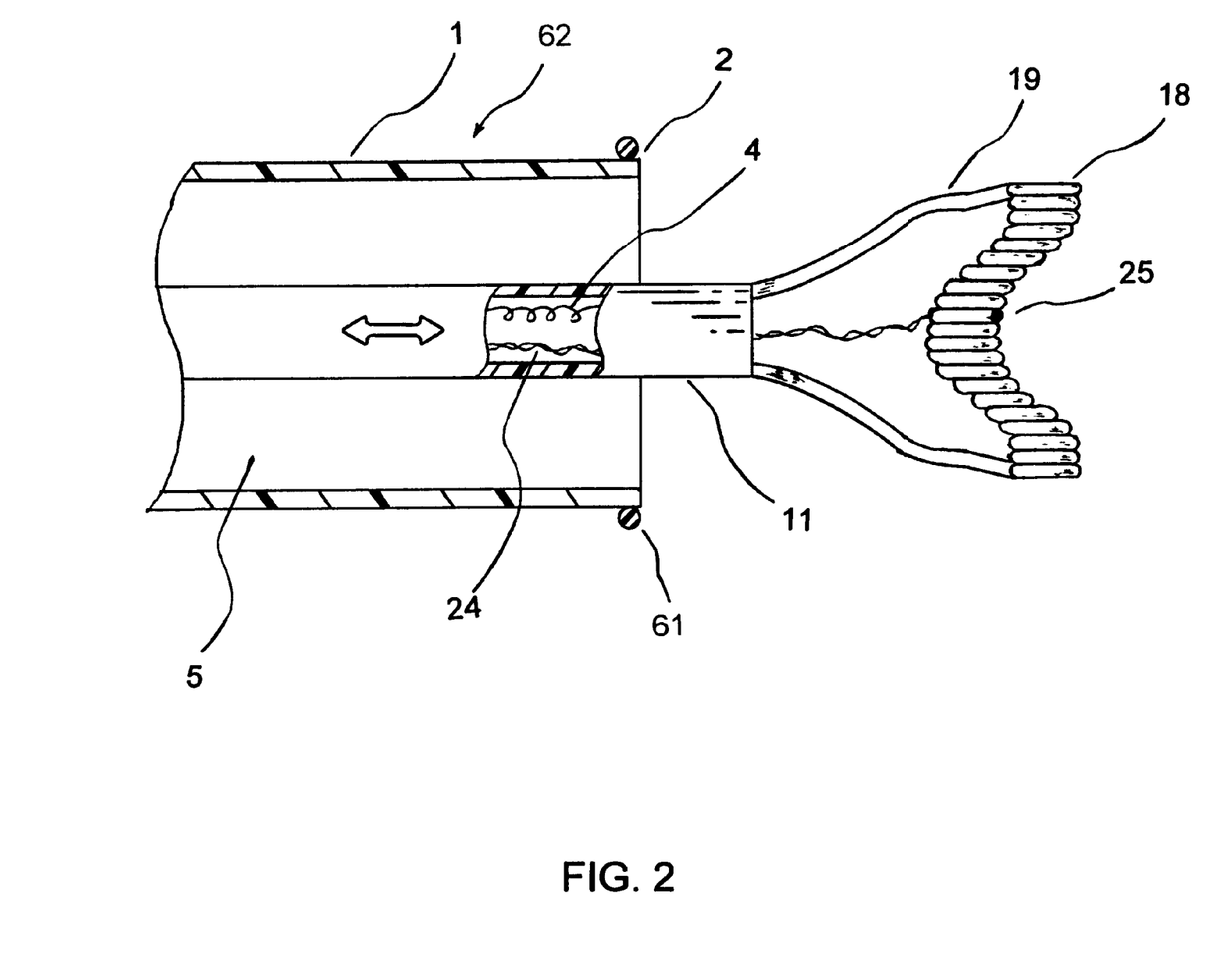
FIG. 2 is a cross-sectional view of the distal end portion of the device, including a concave-top coil electrode arrangement and a dilated ligature element for applying the pressure therapy to the medical device in FIG. 1.
Figure 4:
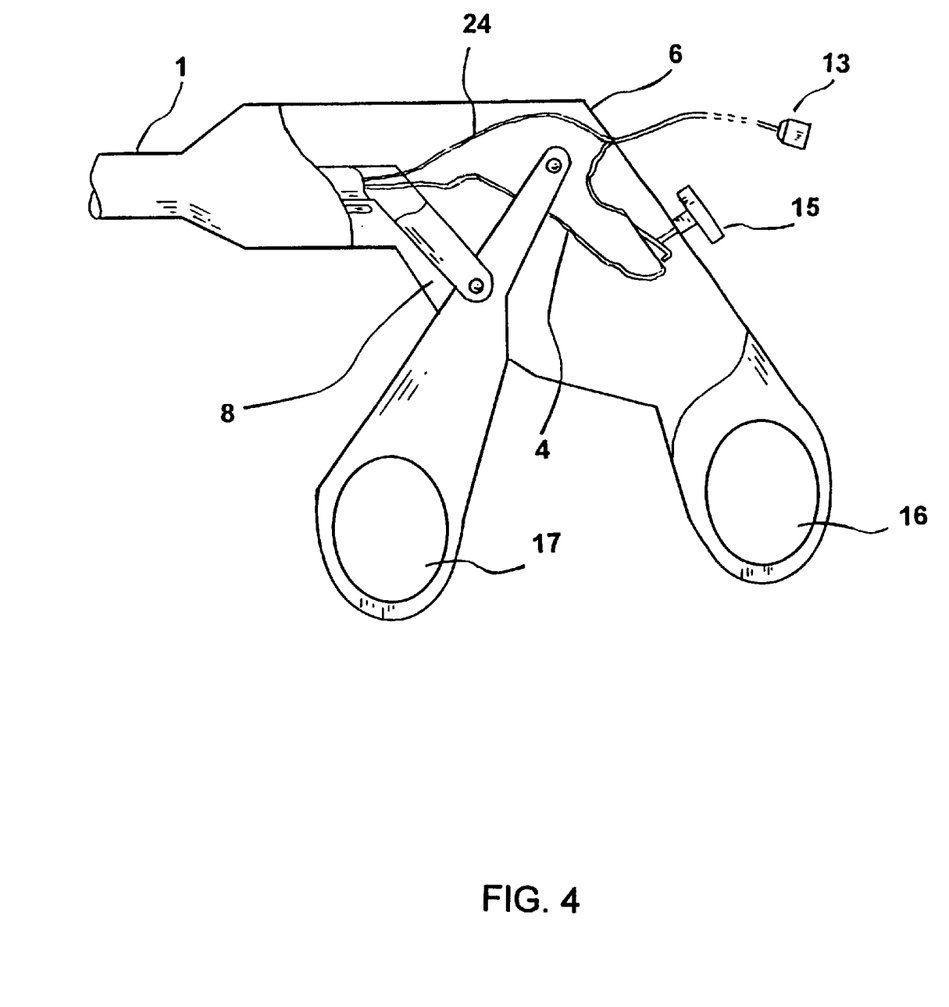
FIG. 4 is a cross-sectional view of the handle portion of FIG. 1.

As shown in FIGS. 1, 2, and 4 the medical device in the form of an elongate tubular assembly comprises a delivery tubular shaft 1 having a distal section 62, a distal end 2, a proximal end 3, and at least one lumen 5 extending therebetween. A handle 6 is attached to the proximal end 3 of the delivery tubular shaft 1, wherein the handle 6 has a cavity 8. An inner elongate tubular shaft 11 is located within the at least one lumen 5 of the delivery tubular shaft 1. In one embodiment, the delivery tubular shaft 1 and the accompanying inner elongate tubular shaft 11 are semi-flexible and bendable.

FIG. 2 shows a cross-sectional view of the distal end portion of the device, including a concave-top coil electrode 18 for applying the pressure therapy to the medical device. The coil electrode arrangement 18 can be a flatten-top fashion, a convex-top fashion, and the like which is most appropriate to encircle the target tissue. The inner elongate tubular shaft 11, on which thereof an electrode means 18, is mounted on a distal end portion 19, which surface may be insulated. An insulated electrical conductor 4 passes through the shaft 11 and is connected to the electrode means 18. The other end of the electrical conductor is externally connected to an energy source.

A dilated ligature element 61 may be detachably mounted at the distal section 62 of the delivery tubular shaft 1. In one embodiment, the very distal end portion of the distal section 62 may comprise a circumferential trough or groove for positioning the dilated ligature element 61 during the non-deployed state or during the device insertion step. A conventional pushing mechanism for deploying the dilated ligature element 61 forward may become an integral part of the present device. This pushing operation is used to deploy the ligature element out of the distal end of the catheter shaft 1 and the electrode arrangement 18.

Figure 3:
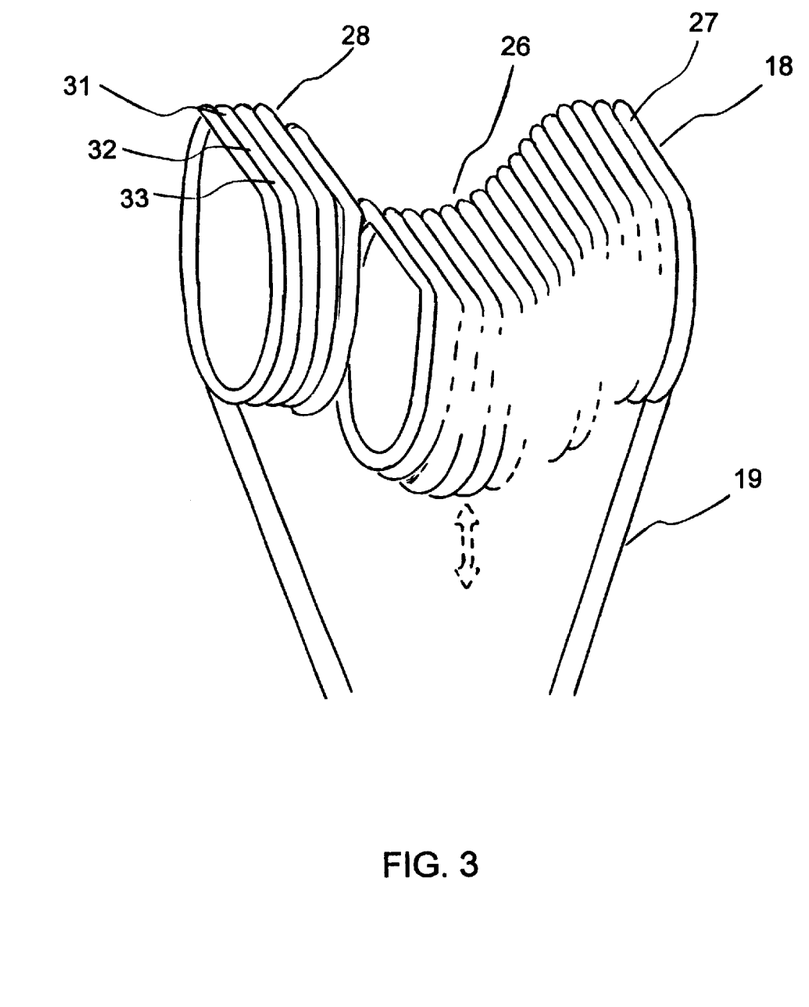
FIG. 3 is a perspective view of a compressible, concave-top coil arrangement at the distal end of the medical device of the present invention.
Figure 5:
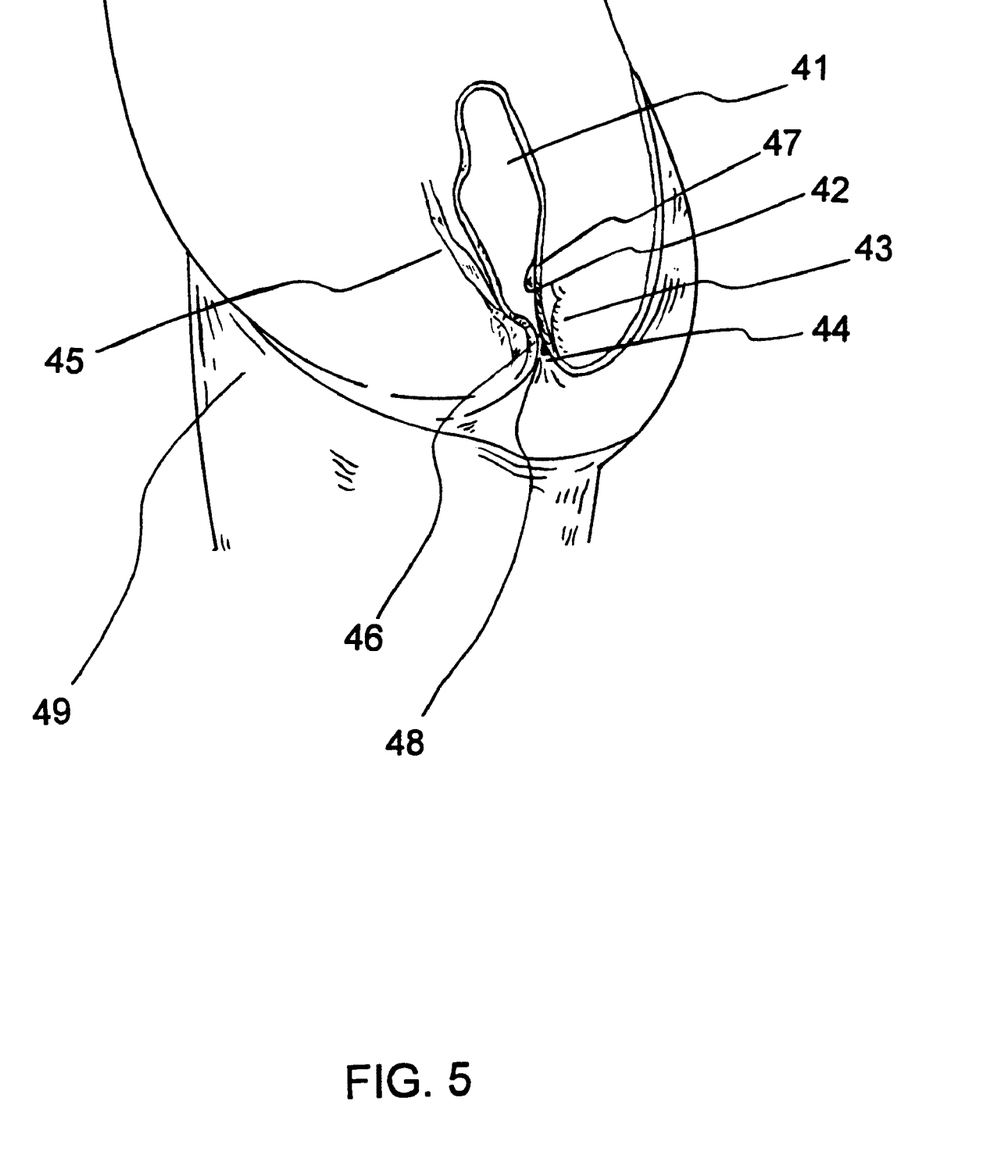
FIG. 5 is an illustrative side-view of the anal canal and hemorrhoids to be treated by the medical device of the present invention.
Figure 6:
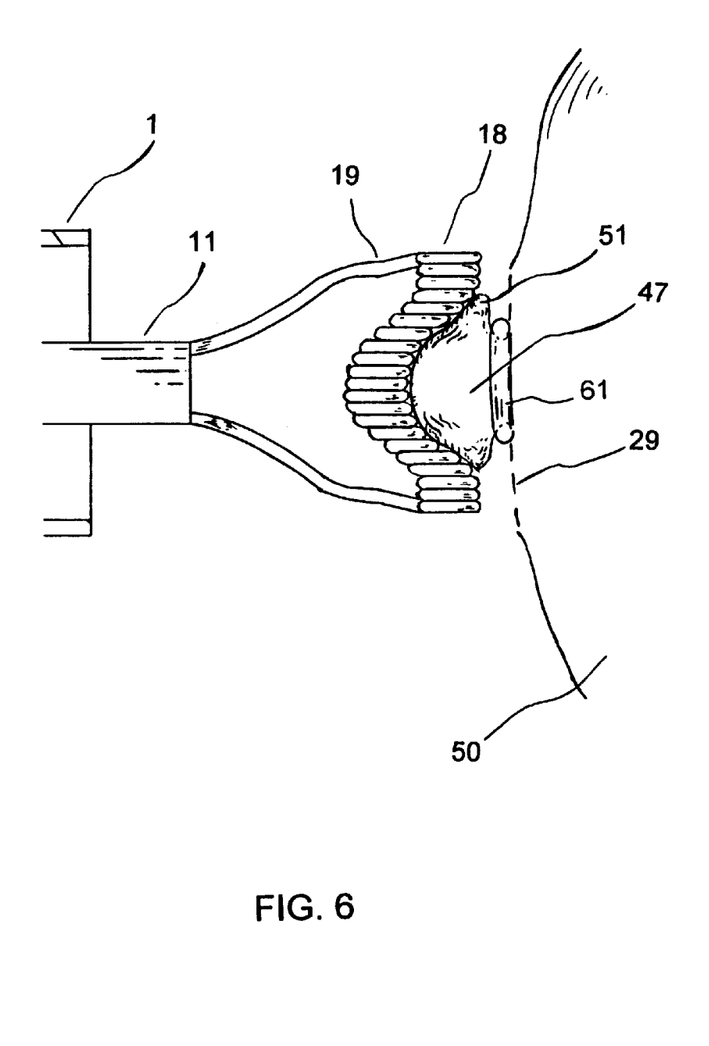
FIG. 6 shows a perspective view of a hemorrhoid region being treated by the medical device of the present invention.

FIGS. 3, 5 and 6 shows a perspective view of a compressible, concave-top coil loop arrangement at the distal end of the medical device. The electrode means 18 comprises at least one compressible coil loop arrangement having a distal end portion 26, 27, 28 to contact a target tissue 47. The compressible coil loop arrangement has the capability of applying appropriate pressure to encircle and press the target tissue in the longitudinal direction along with the elongate tubular shaft 11. In one embodiment, the distal end portion of the compressible coil loop arrangement may be shaped in a flatten-top or convex-top fashion relative to the target tissue and adapted to maximize the contact with the target tissue.

This concave-top fashion is illustrated in FIG. 3 including the edge coils 27 and 28, and the center coil 26, which is at the bottom of the concave fashion. In another embodiment, the distal end portion of the compressible coil loop arrangement is shaped in a flatten-top fashion relative to the target tissue and adapted to maximize the contact with the target tissue. This flatten-top fashion is illustrated in FIG. 3, including the flattop surface points 31, 32, and 33 on the same coil of the coil loop arrangement. Alternately, the distal end portion of the at least one compressible coil loop arrangement is shaped in a convex-top fashion relative to the target tissue and adapted to maximize the contact with the target tissue, wherein the target tissue is encircled by an inner surface of said convex-top compressible coil loop arrangement.

FIG. 4 shows a cross-sectional view of the handle portion 6 of the present invention. The handle 6 comprises a cavity 8 and holders 16 and 17 for the thumb and finger so that the inner elongate tubular shaft 11 can be deployed with ease. The electricity of the electrical conductor 4 is controlled through an on-off control knob 15 to selectively deliver RF energy to the electrode means 18.

The device system comprises an external RF energy generating means (not shown), wherein the RF energy is provided to the electrode means 18 through the electrical conductor 4. A connector 13 is secured to the proximal end of the handle 6. The RF energy is supplied from an external RF energy generating means through an on-off knob 15 to control the RF energy delivery to the electrode means 18. The handle 6 has a thumb holder 16 and a finger holder 17 to guide the device to the appropriate location of the target tissue site. The finger holder 17 also serves as a delivery controller. The inner elongate tubular shaft 11 is deployed out of the delivery tubular shaft 1 and retracted to remain inside the delivery tubular shaft 1 by the control mechanism of the delivery controller 17.

The connector 13 comprises several pins for connecting an electrical conductor 4, and a temperature sensing wire 24 to external instruments, such as a RF generator, an EKG monitor, and/or a temperature control mechanism.

In one embodiment, at least one temperature sensor 25 is disposed at close proximity of the electrode means 18. Insulated temperature sensor wire means 24 passes from the temperature sensor 25 at the distal end portion, to an external temperature controller through the outlet connector 13. The RF energy delivery is controlled by using the measured temperature from the temperature sensor 25, through a closed-loop temperature controller and/or algorithm. When the measured temperature rises to the preset high-limit point, the temperature controller sends out a signal to cut off the RF energy supply. In a similar manner, when the measured temperature drops to the preset low-limit point, the temperature controller sends out a signal to activate the RF energy supply.

FIG. 5 shows a perspective view of a hemorrhoid region being treated by the medical device of the present invention. For illustrative purposes, the thigh 49 and the groin section of the body is shown in FIG. 5. The lower part of the rectum 41 is confined by sphincter ani internus 42 and sphincter ani externus 43. A pectinate line 46 separates the rectum 41 from the exterior portion of the body, wherein the opening for the rectum is the anal canal 44. An internal hemorrhoid 47 and an external hemorrhoid 48 are also shown to illustrate their relative anatomical location for ablation purposes.

During procedures, the medical device is inserted into the rectum through an anal canal 44. A method of treating a hemorrhoid of a patient, the method comprises: (a) placing a medical device system against the hemorrhoid of the patient, wherein the medical device comprises a delivery tubular shaft having a distal section, a distal end, a proximal end, and at least one lumen extending therebetween; a handle attached to the proximal end of the delivery tubular shaft, wherein the handle has a cavity; an inner elongate tubular shaft located within the at least one lumen of the delivery tubular shaft, the inner elongate tubular shaft, on which thereof an electrode means is mounted on a distal end portion, an electrical conductor passing through the inner elongate tubular shaft and connected to the electrode means, and mounted on a proximal end portion of the delivery tubular shaft to the handle of the device, wherein the electrode means comprises at least one compressible coil loop arrangement having a distal end portion to contact a target tissue, the compressible coil loop arrangement having the capability of applying appropriate pressure to encircle and press the target tissue; an elastic dilated ligature element circumferentially and externally positioned at about the distal section of the delivery tubular shaft, wherein said dilated ligature element is pushed off the distal section of the delivery tubular shaft at a deployed state; and a RF energy generating means, wherein the RF energy is provided to the electrode means through the electrical conductor; (b) applying an appropriate pressure on the at least one compressible coil loop arrangement to encircle and press the target tissue; (c) deploy the dilated ligature element to be off the distal section of the delivery tubular shaft; and (d) applying RF energy to the tissues encircled under the exposed coil loop region to effect treatment of the hemorrhoid.

FIG. 6 shows a perspective view of a hemorrhoid region being treated by the medical device of the present invention. The hemorrhoid 47 appears as a bump grown out of the tissue wall of the rectum 41. The hemorrhoidal bump 47 rises above the baseline 29 and forms a mound by an excessive internal venous pressure. The vessel wall 51 becomes dilated over a period of time, if not treated in time. The coil loop electrode 18 is in a concave fashion with its essential concave-top encircling the dilated vessel wall 51. When simultaneously applying the pressure from the handle 6 and RF energy to the dilated vessel wall 51, the wall tissue contracts and tightens.

The rubber band or the ligature element 61 can be deployed after the concave-top coil arrangement 18 encircles intimately the hemorrhoidal bump 47. By pushing the delivery tubular shaft 1 forward so that the distal end 2 contacts the outer ring portion 19 of the coil arrangement 18, the dilated ligature element 61 may be pushed out of the distal section 62 of the delivery tubular shaft 1. The ligature element 61 then surrounds and tightens the base of the hemorrhoidal bump 47 for applying one type of the pressure therapies.

The external RF energy generator means has the capability to supply RF energy by controlling the time, power, delivery mode, and temperature through an optional separate closed-loop temperature controller. The patient is connected to the RF generator means through a DIP electrode to form a closed-loop current system. Therefore, RF energy is applied and delivered to the targeted hemorrhoid region, through the electrode means of this invention. The radiofrequency energy current in this invention is preferably within the range of 50 to 2,000 kHz. The frequency of the vibration of the medical device in this invention is preferably within the range of 60 to 1000 cycles per minute. By simultaneously applying RF energy to the electrode and by applying the pressure therapy, the hemorrhoid can be treated.

In a particular embodiment, the material for the electrode means of this invention consists of conductive metals such as platinum, iridium, gold, silver, stainless steel, Nitinol, tungsten, copper, or an alloy of these metals.

In summary, a method of treating a hemorrhoid of a patient comprises ligating a hemorrhoid tissue and heating the hemorrhoid tissue. The heating may be accomplished by a heat source positioned adjacent the hemorrhoid tissue. The heating step comprises treating the hemorrhoid tissue with radiofrequency energy, infrared energy, microwave energy, laser energy, and the like.

From the foregoing description, it should now be appreciated that a device system for the hemorrhoid and the treatment of vascular tissues, comprising a suitable energy source and a pressure therapy of a ligation element has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A medical device system comprising:

a delivery tubular shaft having a distal section, a distal end, a proximal end, and at least one lumen extending therebetween;

a handle attached to the proximal end of the delivery tubular shaft, wherein the handle has a cavity;

an inner elongate tubular shaft located within the at least one lumen of the delivery tubular shaft, the inner elongate tubular shaft, on which thereof an electrode means for treating tissue is mounted on a distal end portion, an electrical conductor passing through the inner elongate tubular shaft and connected to the electrode means, and mounted on a proximal end portion of the delivery tubular shaft to the handle of the device, wherein the electrode means comprises at least one compressible coil loop arrangement having a distal end portion to contact a target tissue, the compressible coil loop arrangement having the capability of applying appropriate pressure to encircle and press the target tissue;

an elastic dilated ligature element circumferentially and externally positioned at about the distal section of the delivery tubular shaft, wherein said dilated ligature element is pushed off the distal section of the delivery tubular shaft at a deployed state; and a RF energy generating means, wherein the RF energy is provided to the electrode means through the electrical conductor.

2. The medical device system of claim 1, wherein the delivery tubular shaft and the inner elongate tubular shaft are semi-flexible and bendable.

3. The medical device system of claim 1, wherein the distal end portion of the at least one compressible coil loop arrangement is shaped in a concave-top fashion relative to the target tissue and adapted to maximize the contact with the target tissue.

4. The medical device system of claim 1, wherein the distal end portion of the at least one compressible coil loop arrangement is shaped in a convex-top fashion relative to the target tissue and adapted to maximize the contact with the target tissue, wherein the target tissue is encircled by an inner surface of said convex-top compressible coil loop arrangement.

5. The medical device system as in claim 1 further comprising at least one temperature sensor, wherein the temperature sensor is disposed at close proximity of the electrode means of the device system.

6. The medical device system as in claim 5 further comprising a temperature controller, wherein the temperature measured from the temperature sensor is relayed to the temperature controller and adapted to effect the RF energy supply to the medical device.

7. The medical device system of claim 1, wherein the RF energy is within the range of 50 to 2,000 kHz.

8. The medical device system of claim 1, wherein the at least one compressible coil loop arrangement of the electrode means is selected from the group consisting of platinum, iridium, gold, silver, stainless steel, Nitinol, tungsten, copper, or an alloy of their mixtures.

9. A method of treating a hemorrhoid of a patient, the method comprising:

(a) placing a medical device system against the hemorrhoid of the patient, wherein the medical device comprises a delivery tubular shaft having a distal section, a distal end, a proximal end, and at least one lumen extending therebetween; a handle attached to the proximal end of the delivery tubular shaft, wherein the handle has a cavity; an inner elongate tubular shaft located within the at least one lumen of the delivery tubular shaft, the inner elongate tubular shaft, on which thereof an electrode means for treating tissue is mounted on a distal end portion, an electrical conductor passing through the inner elongate tubular-shaft and connected to the electrode means, and mounted on a proximal end portion of the delivery tubular shaft to the handle of the device, wherein the electrode means comprises at least one compressible coil loop arrangement having a distal end portion to contact a target tissue, the compressible coil loop arrangement having the capability of applying appropriate pressure to encircle and press the target tissue; an elastic dilated ligature element circumferentially and externally positioned at about the distal section of the delivery tubular shaft, wherein said dilated ligature element is pushed off the distal section of the delivery tubular shaft at a deployed state; and a RF energy generating means, wherein the RF energy is provided to the electrode means through the electrical conductor;

(b) applying an appropriate pressure on the at least one compressible coil loop arrangement to encircle and press the target tissue;

(c) deploy the dilated ligature element to be off the distal section of the delivery tubular shaft to ligate the hemorrhoid; and (d) applying RF energy to the tissues encircled under the exposed coil loop region to effect treatment of the hemorrhoid.

10. The method of treating a hemorrhoid of a patient as in claim 9, wherein the distal end portion of said at least one compressible coil loop arrangement is shaped in a concave-top fashion relative to the target tissue and adapted to maximize the contact with the target tissue.

11. The method of treating a hemorrhoid of a patient as in claim 9, wherein the distal end portion of the at least one compressible coil loop arrangement is shaped in a convex-top fashion relative to the target tissue and adapted to maximize the contact with the target tissue, wherein the target tissue is encircled by an inner surface of said convex-top compressible coil loop arrangement.

12. The method of treating a hemorrhoid of a patient as in claim 9, the method further comprising the medical device system comprising at least one temperature sensor, wherein the temperature sensor is disposed at close proximity of the electrode means of the medical device system.

13. The method of treating a hemorrhoid of a patient as in claim 12, the method further comprising the medical device system comprising a temperature controller, wherein the temperature measured from the temperature sensor is relayed to the temperature controller and adapted to effect the RF energy supply to the medical device system.

14. The method of treating a hemorrhoid of a patient as in claim 9, the method further comprising the medical device system having the RF energy delivery within the range of 50 to 2,000 kHz.

15. A method of treating a hemorrhoid of a patient comprising ligating a hemorrhoid tissue and heating the hemorrhoid tissue, wherein said heating step comprises treating said hemorrhoid tissue with an energy source selected from a group consisting of radiofrequency energy, infrared energy, microwave energy, or ultrasound energy.

* * * * *